US007855656B2

(12) United States Patent
Maschke (10) Patent No.: US 7,855,656 B2
(45) Date of Patent: Dec. 21, 2010

(54) METHOD FOR MONITORING MOVEMENT WITH A MEDICAL INSTALLATION AND ASSOCIATED MEDICAL INSTALLATION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 312 days.

(21) Appl. No.: 12/148,549

(22) Filed: Apr. 18, 2008

(65) Prior Publication Data

US 2008/0258929 A1  Oct. 23, 2008

(30) Foreign Application Priority Data

Apr. 20, 2007  (DE) .................. 10 2007 018 810

(51) Int. Cl.
*G08B 21/00* (2006.01)
(52) U.S. Cl. ............... 340/686.1; 340/686.6; 340/573.1
(58) Field of Classification Search .......... 340/686.1, 340/686.2, 686.6, 573.1, 573.5, 572.1, 539.12, 340/539.13, 539.23; 378/21, 65, 196; 600/407, 600/424
See application file for complete search history.

(56) References Cited

U.S. PATENT DOCUMENTS

| 5,042,486 | A | 8/1991 | Pfeiler et al. | |
|---|---|---|---|---|
| 6,298,261 | B1 | 10/2001 | Rex | |
| 6,498,944 | B1 * | 12/2002 | Ben-Haim et al. | 600/407 |
| 7,657,301 | B2 * | 2/2010 | Mate et al. | 600/424 |
| 2004/0002641 | A1 * | 1/2004 | Sjogren et al. | 600/407 |
| 2005/0215887 | A1 * | 9/2005 | Ben-Haim et al. | 600/424 |
| 2006/0247520 | A1 * | 11/2006 | McGee | 600/434 |
| 2007/0078334 | A1 * | 4/2007 | Scully et al. | 600/424 |
| 2007/0238984 | A1 | 10/2007 | Maschke et al. | |
| 2008/0240363 | A1 | 10/2008 | Grebner et al. | |

FOREIGN PATENT DOCUMENTS

| DE | 36 16 389 A1 | 11/1987 |
|---|---|---|
| DE | 693 27 436 T2 | 3/1994 |
| DE | 4436828 C1 | 3/1996 |
| DE | 196 25 409 | 1/1998 |
| DE | 19852467 A1 | 7/1999 |
| DE | 100 25 285 A1 | 12/2001 |
| DE | 102 00 534 A1 | 7/2003 |
| DE | 10 2004 041 821 A1 | 3/2006 |
| DE | 102005012700 A1 | 9/2006 |
| DE | 10 2005 028 215 A1 | 12/2006 |
| DE | 102005034167 A1 | 2/2007 |
| WO | WO 2006/025003 A1 | 3/2006 |

OTHER PUBLICATIONS

Siemens AG; "AXIOM Artis dFA DynaCT, A breakthrough in interventional 3D imaging"; © 2005 Siemens Medical Solutions, 2005, pp. 1-2, Order No. A91100-M1400-D159-10-7600, Printed in Germany 91/4/6093 WS 04055.

* cited by examiner

*Primary Examiner*—Van T. Trieu (57) ABSTRACT

The invention relates to a method for monitoring the movement of at least one mobile object with a medical installation. A current three-dimensional position of the at least one mobile object is detected by at least one position sensor that is arranged on the at least one mobile object. The invention also relates to the associated medical installation.

16 Claims, 4 Drawing Sheets

METHOD FOR MONITORING MOVEMENT WITH A MEDICAL INSTALLATION AND ASSOCIATED MEDICAL INSTALLATION

CROSS REFERENCE TO RELATED APPLICATIONS

This application claims priority of German application No. 10 2007 018 810.4 filed Apr. 20, 2007, which is incorporated by reference herein in its entirety.

FIELD OF THE INVENTION

The invention relates to a method for monitoring movement with a medical installation and the associated medical installation.

BACKGROUND OF THE INVENTION

Medical installations, which are used, for example, for imaging diagnosis or for therapies, such as angiographic equipment and radiation therapy equipment, very frequently comprise mobile device parts which are arranged in the examination room. These device parts are moved by automatic or at least partially automatic or manual control. One example to mention is a C-arm in X-ray units or patient tables.

The movement of the device parts of medical installations of this kind is partially achieved by means of high-power drive units. The mobile device parts can therefore, for example in the case of carelessness on the part of the operator, injure or damage the patient, other parts of the installation or other people, in particular in the event of a collision with a heavy or fast-moving device part. This is in particular problematic with those modern systems in which there is a plurality of possible movements of the individual installation parts, which are difficult to assess at first glance. Hereby, collisions can result in serious damage or injuries.

Nowadays, it is normal for the operator, that is, for example, an imaging technician or a correspondingly trained doctor, to perform a slow preliminary examination and thereby ensure that no collision occurs. The imaging or examination or therapy is then performed in real time.

Known from DE 102 00 534 is a method for the collision-free movement of at least two objects that can be moved toward each other in which the sequence of movement is simulated on a screen. The operator is shown any possibly risky movement sequences. The simulation relates to the components of an examination device.

Also known is a device for X-ray examination with an arrangement for preventing collisions according to DE 693 27 436. With this device, in the event of a collision, the increase in the power of an electromotive drive unit is determined and thereby a collision recognized by comparison with a threshold value.

The medical installation in DE 196 25 409 offers the possibility of using a neuronal network to monitor the individual components of a medical installation with respect to the risk of a collision. This enables the components of the medical installation known to the system control to be detected. Further devices and equipment in the area such as tool trolleys or people and other objects and the patient are not detected.

WO 2006/025003 describes the possibility of attaching a capacitive layer to a moving X-ray stand which changes as an object is approached and which recognizes a collision via downstream electronics.

However, all these systems have drawbacks to the effect that a collision first has to take place, so that a movement is interrupted or that only certain parts of the medical installation are included in the monitoring. There is no protection for other devices or people.

SUMMARY OF THE INVENTION

Therefore, the invention is based on the object of disclosing a method of the type described in the introduction which has been improved in this respect.

To achieve this object, with a method for monitoring the movement of at least one mobile object with a medical installation, the current three-dimensional position of the object is detected by means of at least one position sensor arranged on the at least one mobile object.

Therefore, position sensors will be or are attached to the objects, for example, an X-ray component, a patient's bed, a respirator or trolley or even a tool table, to the operating staff or patient, which are then detected in their three-dimensional assignment in the area, to which end corresponding receiver devices are provided in the region of the installation, for example, or also on the objects.

Unlike the known solutions, for example including a solution working with proximity switches which interrupt the movement when activated, the invention has the advantage that a collision does not actually have to have taken place for this or the risk of this to be recognized, with it being simultaneously possible to protect not only certain specified components of the installation, but further devices such as trolleys and people.

If the fixed position of a plurality of objects provided with position sensors or for example a computation apparatus are known, the three-dimensional positions can be detected or used for all the respective objects or for a plurality of objects and from these the relative positions calculated which represent the risk of a collision. This can be performed by means of a corresponding computation apparatus. The actual position detection is performed by means of one or more receiving units for signals from the sensor or sensors. Due to the spatial position detection, i.e. the three-dimensional assignment, it is possible reliably to avoid collisions with respect to the variety of possible movements that exist with people and also with modern medical installations.

The position can be detected by means of at least one position sensor on a component of the medical installation, in particular on a component of an X-ray system and/or a patient's bed and/or a respirator and/or a trolley and/or a tool table, and/or a person, in particular an operator and/or a patient, as an object.

Hence, according to the invention, it is possible that a wide variety of objects will be or are provided with position sensors. This does not necessarily have to be parts which are permanently assigned to an installation such as, for example, a C-arm, it is also possible to detect mobile parts which are not always present in the area of the installation such as for example respirators.

In addition, it is possible to protect people with the method according to the invention. Hereby, it is also possible for an object, that is, for example, a device or a person, to be provided with more than one position sensor in order reliably to detect the plurality of possible movements whereby it is also possible for the position of different components or regions of an object relative to each other to change. For example, it is possible that the position of an X-ray emitter relative to the detector or that of a suspension to the C-arm could change. In such a case, the emitter and the detector and the suspension and parts of the suspension connected by articulated joints can each be provided with their own position sensors. The position detection by means of the position sensors can hereby take place when the object is moving or idle.

Hence, the method according to the invention offers comprehensive monitoring of movement and not merely collision avoidance in the narrower sense. It is possible at all times to locate a position sensor on an object and hence the three-dimensional position of the object. It is therefore possible to identify or predict any possible risk in advance and in real time.

The position of the at least one object can be detected continuously or at time intervals. Therefore, the three-dimensional spatial position of the object can be determined continuously in real time. In addition, it is additionally or alternatively possible, to check the spatial position of a person or a device at certain time intervals. For example, the position can be checked every 10 seconds, which in particular enables the computation effort to be reduced in particular for the determination of the position relative to other mobile objects. Continuous position detection is advantageous in the case of objects exposed to rapid movements, at least during a movement of this kind. In conjunction with detection at intervals for objects which are moved only rarely or slowly, this continuous position detection can then be sufficient to reliably detect the movement in such a way that collisions are reliably excluded.

The three-dimensional position of the at least one object can be detected by means of at least one receiving device for signals of the at least one position sensor. Optionally, a plurality of receiver devices can be present, for example in order to improve the accuracy of the position detection or in order to receive signals from different sensors optionally at different spatial positions.

An evaluation unit can be used to determine the position of at least one mobile object relative to at least one further mobile and/or spatially fixed object, in particular in dependence on the position detection by at least one receiving device. For example, it is possible by means of the evaluation unit, which can substantially be a computing system, to determine the position for example of an X-ray emitter or of the position sensor arranged thereon relative to a person or another component of the installation. For this, it is possible to use the data from the receiving device or plurality of receiver devices which for this purpose can be supplied to the evaluation unit via a suitable data connection. This position determination can take place automatically. Alternatively or additionally, an operator can specify that the relative position should only be determined for certain components or objects or be calculated particularly frequently for these.

In dependence on the violation of a limit value for the relative position during a movement of the mobile object, it is possible for an alarm to be issued and/or the movement slowed down and/or at a user interface, in particular the evaluation unit, for feedback to be issued, in particular in the form of forced feedback, and/or the movement stopped and/or at least one further measure for collision avoidance performed, in particular by the evaluation unit.

Therefore, if the first mobile object is actually set into motion, on the violation of a limit value for the relative position or in the case of a value for the relative distance to another object being too low from the start, an alarm can be issued, for example. This alarm can be an acoustic or optical alarm. It is also possible, for example, for an acoustic alarm to be issued in combination with an optical alarm. It is also possible for further alarm possibilities to be provided, for example an alarm by means of a tactile signal or the like. In addition, by means of a computation apparatus, for example a computation apparatus of the evaluation unit, the movement can be automatically slowed down or stopped completely. Further measures are also conceivable, such as, for example, a textual or graphical message in software operated by an operator, performing imaging for example, via a user interface. Also possible as feedback or an alarm is tactile forced feedback, which can also inform an operator that a collision is possible or could be imminent. These measures or alarms can be performed by the evaluation unit. In this way a fully automatic alarm is possible. In the case of further measures such as, for example, movement being stopped, prior feedback can be requested from an operator, who in such a case can check once again whether, for example, it is actually advisable to terminate the imaging or whether the relative distance is in fact no longer acceptable.

In addition, it is possible to determine a plurality of limit values for the relative position, with, in dependence on the violation of the respective limit values for the relative position, different measures for collision avoidance being performed.

For example, on the violation of a first, second or third or further limit value, measures can be taken gradually, which are expediently increasingly far-reaching in order reliably to avoid a collision. For example, first an alarm can be issued, while on the violation of a further limit value, i.e. when the relative distance to another fixed or mobile object has become even smaller, the movement is slowed down or a more distinct alarm is issued or the like. The alarm can also be issued for example at decreasing time intervals. In the case of acoustic signals, it is also possible for the volume of the signal to be increased in dependence on the violation of a further limit value.

Finally, the movement can be stopped or the alarm issued in the form of a permanent signal.

According to the invention, it is therefore possible, in dependence on the violation of a first limit value for the relative position during a movement of the mobile object, for an alarm to be issued and, in dependence on the violation of a second limit value, the movement to be slowed down and/or feedback to be given at a user interface, in particular the evaluation unit, in particular in the form of forced feedback, and, in dependence on the violation of a third limit value, the movement to be stopped, in particular by the evaluation unit. For example, forced feedback can be provided via an operating tool such as a joystick or the like.

Therefore, the range of the alarm or the measures is gradually increased depending on which limit value was violated. In this way, at first only an acoustic or an optical alarm can be issued. If there is a further violation of the limit value, that is an even shorter distance between one object and another, the, for example motor-driven, movement of the moving component can be slowed down or feedback or forced feedback can be given via a user interface, for example a software interface, which is being used anyway to conduct the examination, or via an operating tool for a type of software. Ultimately, the movement can be stopped. Optionally, it is possible to define further limit values which are linked to other measures.

In addition, it is also possible to use at least one cableless movement sensor on the at least one object. Therefore, it is possible that a sensor which does not require a cable connection is or will be arranged on the object so that the movement is not restricted by disruptive cables. Obviously, it is also possible to use cable-based movement sensors, but these should mainly be used with objects which are at the most exposed to smaller or slower movements.

At least one position sensor based on a magnetic and/or electromagnetic and/or electric and/or capacitive and/or inductive and/or optical and/or thermal and/or acoustic principle of operation arranged on the at least one object can be used. One example of a possible sensor is a radio-frequency-identification-sensor (RFID sensor) with a radio-based mechanism of operation. Obviously, it is also possible to use different position-recognizing mechanisms in combination, for example, optical sensors in components in which visual contact to the receiver unit is unproblematic. On the other hand, with other components with a frequently-changing position, it is possible, for example, to use radio principles for the position sensors. In addition, it is possible, to further safeguard the position recognition, to provide position sensors on an object which operate in accordance with different principles of operation.

The basis for this can be systems which enable position recognition of medical instruments and catheters according to electromagnetic or acoustic principles, for example, and with a radio-frequency-identification-transponder (RFID transponder).

According to the invention, at least one position sensor arranged on the at least one object by means of at least one adhesion surface and/or a label and/or a hook and loop strap and/or a mechanical clamp and/or clip and/or screw can be used. It is therefore possible that the position sensor is or will be arranged on the object as a label. In the case of people, arm straps or certain clamps or clips are advantageous. Devices can be provided with screw-on position sensors. Depending upon the type of object involved, i.e. a device component or a person or a device component which has a complicated technical design and with which it is necessary to ensure that the attachment of the position sensor does not result in any functional impairment, it is therefore possible to use different mechanisms of attachment.

In addition, at least one position sensor arranged on the at least one object by means of a pin and/or a needle and/or a hair pin and/or a strap, in particular a sling-on strap, and/or an arm strap and/or integrated in a spectacle frame and/or incorporated in clothing and/or in a mouth guard and/or a head cap can be used. These methods of attachment or possible arrangements are advantageous for sensors for people. In addition, in the case of people, a plurality of sensors can be provided to particular advantage. This applies in particular in the case of patients lying on a bed surrounded by installation parts which could come into contact with a wide variety of regions, for example the head or the extremities or the torso region.

Since in this case, in order to ensure that the examination can be performed, the limit values cannot generally be selected too large, here it makes sense to provide different position sensors from the start to detect the different regions of a patient's body to be protected. This makes it possible to select the limit values for the distances in the required small range.

According to the invention, it is possible that position sensors are or will be arranged on a plurality of objects and the current three-dimensional positions of all objects with position sensors can be detected. It is therefore possible for example to provide an X-ray emitter and an X-ray detector, which can be moved together or relatively, with a position sensor. In addition, the patient, for example, comprises at least one position sensor. Further mobile objects in the area can also be provided with position sensors.

It is then possible to detect the current three-dimensional position of all position sensors and hence the three-dimensional position of the objects provided with these position sensors. This makes it possible, for example, for a corresponding evaluation unit to determine the relative distance or the relative position of all or some of these objects to each other including during the movement of a plurality of objects in order to avoid collisions between a wide variety of objects.

In addition, the and/or an evaluation unit can compare the at least one detected position with movements of components of the medical installation which are stored in a system control and/or performed. The evaluation unit, therefore, receives the position sensor signals from its receiver unit or one or a plurality of receiving units in the region of the medical installation, for example, in accordance with an electromagnetic transponder principle, and in this way detects the position of the objects in the area or in the region of the installation which are equipped with at least one position sensor. For example, movements of components of the medical installation can be stored in the system control in a corresponding database. For example, typical movements or the possible movements existing for a specific object can be retrieved. In addition, alternatively or additionally thereto, the movements actually performed can be used for the comparison.

Depending upon the comparison, it is possible to perform measures for collision avoidance, in particular measures such as those described above, i.e., for example, the issue of an alarm, the slowing-down of a movement, feedback for an operator and the stoppage of movement.

In addition, at least one receiving device arranged on a mobile object can be used. In this case, the catalog of measures with the issue of the alarm and optionally further measures can be performed at a certain received field strength between a position sensor e.g. on another other object and the receiving device or unit. The measures can in turn be initiated by the evaluation unit, which to this end receives the signals from the receiver unit of the individual objects via a suitable data connection, i.e., for example, retrieved or forwarded.

A combination of these two methods, that is a method in which receiver devices are arranged on the mobile objects with a method in which a receiving device is assigned to an evaluation unit, is also possible. In this case, therefore, it is also possible both to measure a received field strength on the objects and to use it for the initiation of the alarm concept and also to access stored and performed movements of the components of the examination and therapeutic device with a subsequent comparison.

As described above, therefore, according to the invention, it is possible e.g. in dependence on a sensor signal detected on the at least one receiving device to perform measures for collision avoidance, in particular in dependence on a received field strength.

The method is suitable not only for medical installations, but also permits collision avoidance with other devices for which it is necessary, for example, for people to be in the vicinity, for operation for example, or which comprise expensive devices for which it is necessary to avoid damage.

In addition, the invention relates to a medical installation with means for monitoring the movement of at least one mobile object, in particular according to a method as described above, in which the medical installation is designed for the detection of the three-dimensional position of the at least one mobile object by means of at least one position sensor arranged on the object.

Therefore, the medical installation comprises movement monitoring based on position sensors. By means of the position sensors, which are preferably present on a plurality of mobile objects and optionally also on fixed objects of the medical installation, it is possible to determine the three-dimensional position of the associated objects. This enables, for example a movement of an X-ray emitter or C-arm or, for example, of a person, in particular of a patient or of operating personnel to be followed in real time. An evaluation unit in the medical installation enables the movements to be calculated and relative distances to be determined, with the relative distances between objects being assigned limit values with which these are compared in order optionally to initiate measures for collision avoidance. These measures can be performed automatically by a computation apparatus in the evaluation unit or after consulting an operator.

In this way, it is possible with the medical installation to include a wide variety of objects such as devices and people in the movement monitoring. These will therefore be detected and reliably protected.

BRIEF DESCRIPTION OF THE DRAWINGS

Further advantages, features and details of the invention can be derived from the following exemplary embodiments and from the drawings, which show.

DETAILED DESCRIPTION OF THE INVENTION

Figure 1:
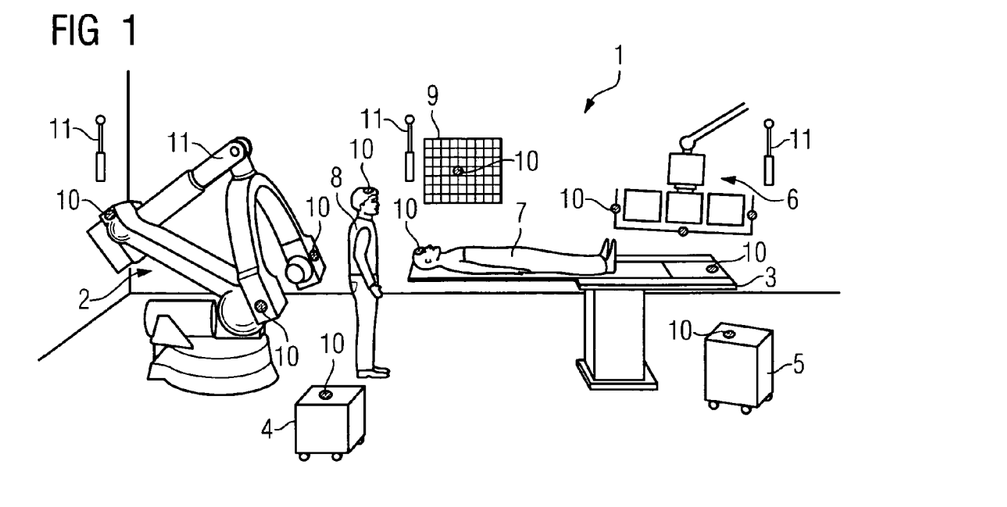
FIG. 1 a medical installation according to the invention.

FIG. 1 shows a medical installation according to the invention 1. The medical installation 1 comprises inter alia an X-ray device 2 with a patient's bed 3. In addition, different medical devices are arranged in the area of the medical installation 1, of which the medical device 4 is shown here by way of example. Like the X-ray device 2 and the patient's bed 3, the medical device 4 is mobile. In addition, in the area of the medical installation 1, there is a tool trolley 5 for medical tools which can be moved on rollers.

A surface-mounted screen matrix 6 can also be turned and swiveled and is therefore a mobile object.

In addition, next to the patient 7, there is an operator 8 in the area of the medical installation 1. Reference number 9 designates a further screen.

Therefore, in the region of the medical installation 1 or in the area of the medical installation 1 shown, there are not only mobile objects which are directly assigned to the medical installation 1, such as, for example, the X-ray device 2, but also mobile objects which, if necessary could also be located in other areas, such as, for example, the medical device 4, which can also used with other installations. The people such as the operator 8 and the patient 7 also represent mobile objects which do not form permanent components of the installation.

With the medical installation 1 shown, all these mobile objects are provided with position sensors 10 or position sensors 10 of this kind are arranged on the objects which then make it possible to assign a three-dimensional position to the mobile objects in the area. For this, a plurality of transmitting/receiving antennas 11 is distributed in the area. The plurality of antennas 11 enable signals from all position sensors 10 to be received reliably and optionally, with recourse to a majority of these antennas 11, the spatial position finding to be improved.

In the present case, the position sensors 10 are RFID transponders. Accordingly, the transmitting/receiving antennas are designed for RFID signals or transmitting antennas for RF energy with corresponding receiving options are used in order to perform position recognition.

A number of the mobile objects, for example the X-ray device 2, are provided with a plurality of position sensors 10 in order in this way to take into account the greater spatial extension of these mobile objects and a plurality of degrees of freedom of movement, which the latter optionally comprise.

With the medical installation 1 according to the invention it is hence possible, by means of an optionally present evaluation unit or software on the basis of the detected three-dimensional positions of the objects to interrupt the movement or take other measures before a collision occurs. The position of all objects in the area can be detected by means of the position sensors 10. This also applies to people and to other components which are not permanently assigned to the medical installation 1, such as, for example, the medical device 4.

Figure 2:
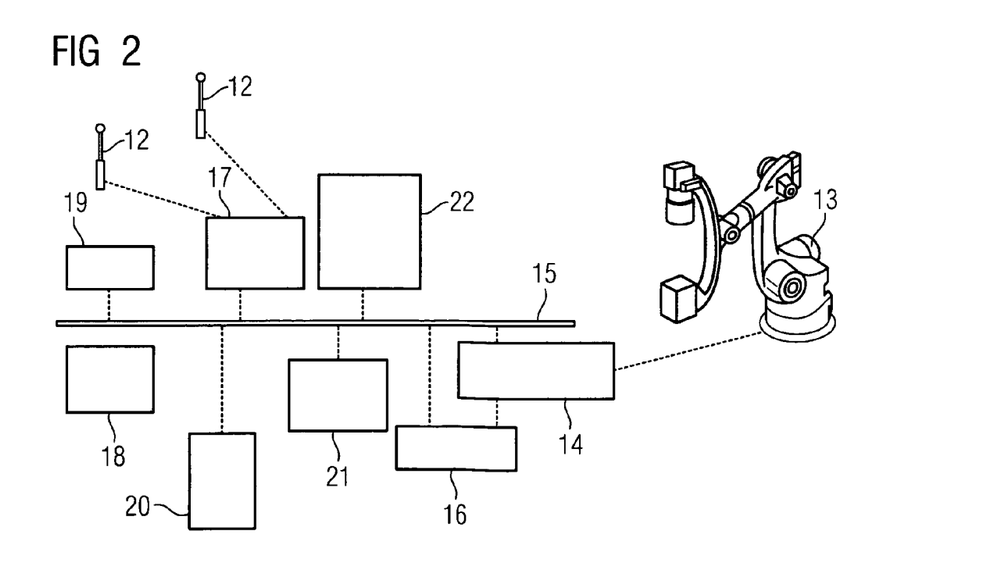
FIG. 2 an illustration of movement monitoring with a method according to the invention, FIG. 3 a position sensor for a method according to the invention, FIG. 4 a further position sensor with a three-dimensional RFID antenna, FIG. 5 an illustration of the principle of position detection with a method according to the invention, FIG. 6 an object with a plurality of position sensors, FIG. 7 a sketch for the definition of different limit values and FIG. 8 an illustration for increasing the accuracy of the position detection with a method according to the invention.

FIG. 2 shows an illustration for monitoring movement with a method according to the invention. This shows a plurality of transmitting/receiving antennas 12, which are antennas for RFID signals or transmitting antennas for RF energy. It also shows an X-ray device 13. The X-ray device 13, which, in other embodiments could also be another examination or therapeutic device, for example an ultrasound device or the like, is connected to a drive control 14 in this case for the X-ray device 13, generally for an examination or therapeutic device. The drive control 14 for the examination or therapeutic device is connected to a data bus 15. There is also a connection to the system control 16, which in turn is coupled to the data bus 15.

The transmitting/receiving antennas 12 are connected to a transmitting/receiver unit 17, a so-called interrogator, which is connected to the data bus 15. Also provided is a general power supply unit 18. A data memory 19 is also connected to the data bus 15.

Operator or user entries can be made via a user input/output unit 20. The antenna signals of the transmitting/receiving antennas 12 are further processed in a processing module 21 in order to permit the assignment of a spatial position. Provided for the movement monitoring is a collision monitoring and evaluation unit 22 specially designed for this, which accesses, for example, the movements of the individual components of the basic medical installation such as the X-ray device 13 or another examination and therapeutic device stored in the system control 16 and optionally performed in each case. The collision monitoring and evaluation unit 22 makes it possible by means of the definition of certain limit values for the distance of the individual components or people in the medical installation relative to each other to monitor the movement continuously or at certain intervals. In dependence on a limit value being approached or the violation of limit values, it is possible to initiate an alarm concept or measures concept, which can, for example, comprise an acoustic or optical alarm, the braking of individual components or feedback with the aid of forced feedback or the stoppage of movements.

While here separate transmitting/receiving antennas 12 are provided, the method according to the invention can alternatively or additionally also be performed with receiving units attached to the components of the examination and therapeutic device. In this case, the alarm concept can be initiated on a corresponding received field strength on approach as a limit value.

Figure 3:
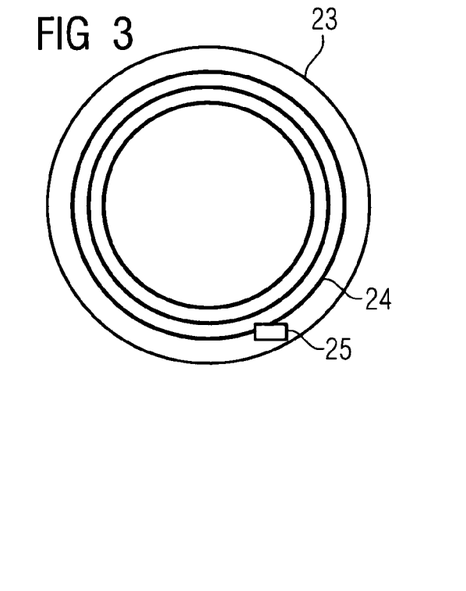

FIG. 3 shows a position sensor 23 as a sticker for use with a method according to the invention. The position sensor 23 comprises a one-dimensional RFID antenna 24 plus an RFID receiving, transmitting and processor unit 25. In this case, therefore, the RFID receiving, transmitting and processor unit 25 is integrated directly in the position sensor 23 so that via this unit 25, the signal field strength can be obtained from received sensor signals in order optionally to initiate an alarm concept in dependence on the received field strength.

A sticker of this kind as a position sensor 23 can be applied flexibly to a wide variety of installation parts and also to people. If new mobile objects are introduced in a area of a medical installation, for example mobile tool trolleys, which are used in different areas of a hospital, these are simply provided with a sticker as a position sensor 23 causing them to be automatically integrated in the concept for movement monitoring. Optionally, information in the software of an evaluation unit such as information on the spatial expansion of the object provided with the sticker can be supplemented or, if this is already stored, retrieved in order to optimize the position monitoring. It is conceivable, for example, that an operator will enter information of this kind on corresponding input fields or the like in the software. In dependence on this information, it is possible to define limit values which are decisive for the alarm concept.

Figure 4:
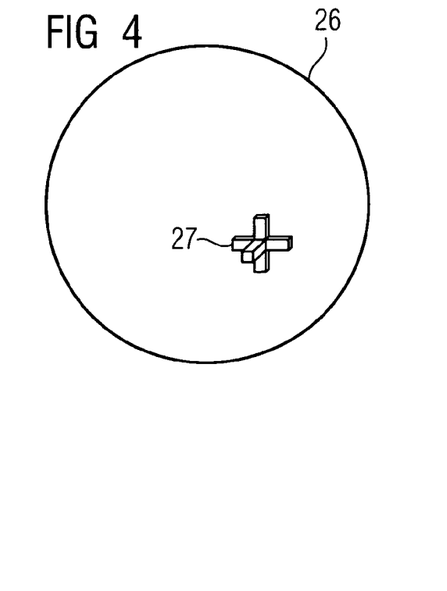

FIG. 4 shows a further position sensor 26, which is a position sensor 26 equipped with a three-dimensional RFID antenna 27. The position sensor 26 is in turn designed as a sticker.

The three-dimensional RFID antenna 27 is a micro RFID receiving/transmitting unit, with which the transmission and reception of RFID signals in the x-, y- and z-directions is possible. This enables three-dimensional position recognition in the area, with the three-dimensional RFID antenna according to the invention simultaneously being used for the reception of signals from other position sensors and for the transmission of its own signals.

Figure 5:
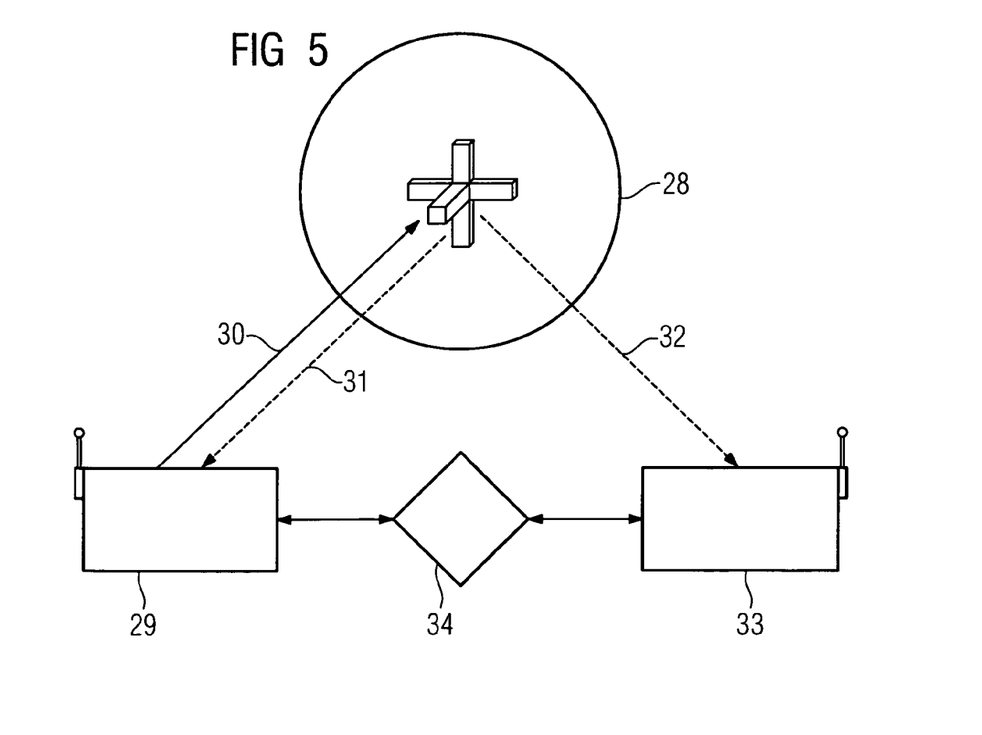

FIG. 5 shows an illustration of the principle of position detection with a method according to the invention. In the case shown, the identification is again performed by means of RF signals (radio-frequency signals) in interaction with magnetic position finding. In the center, there is a micro RFID receiving/transmitting unit 28 with a three-dimensional design for the x-, y- and z-directions. As indicated by the arrow 30, a transmitter and interrogator 29 transmit a RF information signal and RF energy to the unit 28. The unit 28 in turn returns an RF information signal to the transmitter and interrogator 29 as indicated by the arrow 31. In addition, the micro RFID receiving/transmitting unit 28 sends a signal to a magnetic field sensor 33 as indicated by the arrow 32. The transmitter and interrogator 29 and the magnetic field sensor 33 are in turn connected to each other by a processor 34. It this way it is possible to determine the three-dimensional spatial position of an object provided with a sensor with the unit 28, e.g. in the form of a sticker or tape.

Figure 6:
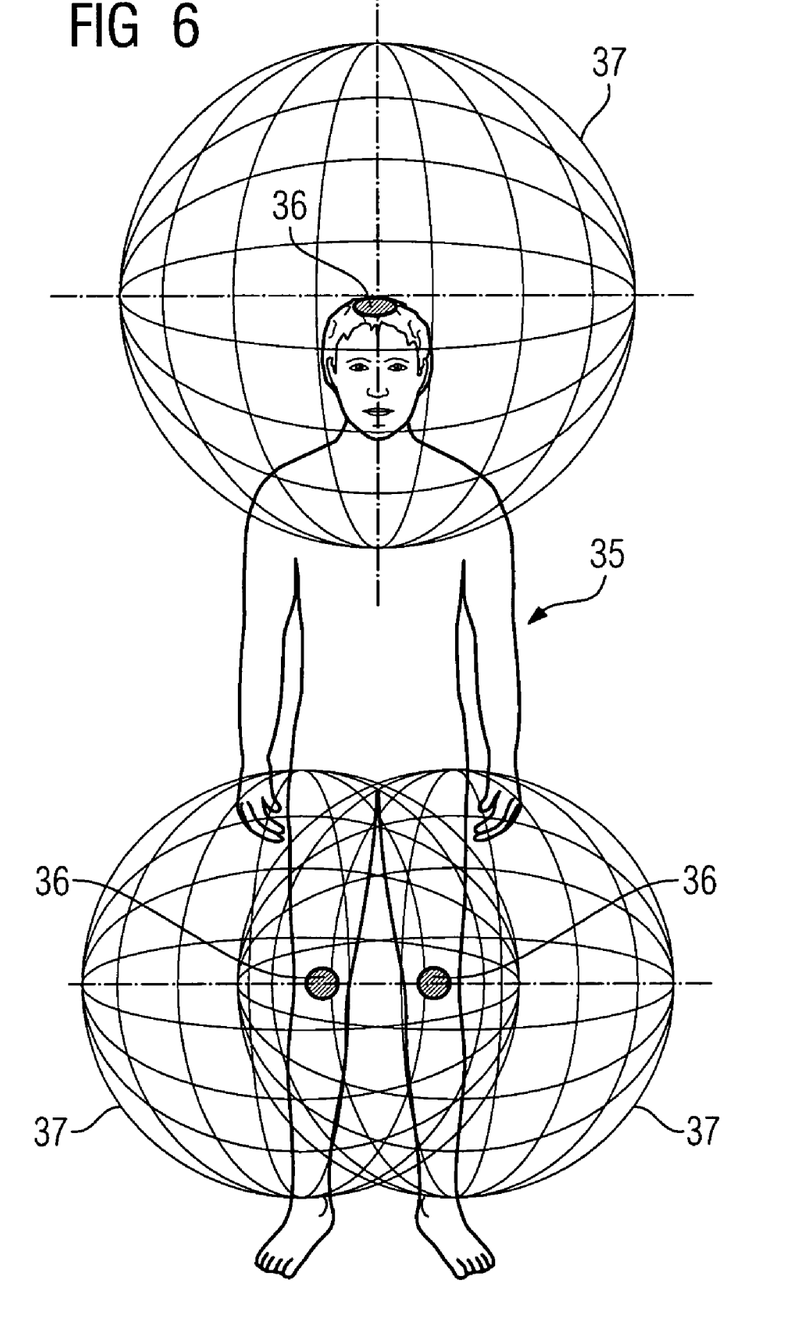

FIG. 6 shows an object 35 with a plurality of position sensors 36. In the case shown, the object 35 is a person wearing a position sensor 36 in the region of the head and two further position sensors 36 in the region of the left and right legs. Protection zones 37 are defined around respective position sensors 36. The shape and size of the protection zones 37 can be selected so that the entire object 35 or, as here, a region at risk with respect to collisions is covered by means of these protection zones 37. The protection zones 37 are used to specify limit values for taking measures or an alarm concept. If another object in the region is located in the protection zones 37 or enters a protection zone 37, optionally warnings are issued or measures taken, which could, for example, consist in the fact that the movement of the other object, for example a C-arm for X-ray images is slowed down. If still further position sensors 36 are applied to the object 35, it is optionally possible to define the protection zones 37 as smaller so that a further approach of other mobile objects is possible without this initiating the alarm concept. This makes it possible to enable or detect finer movements and nevertheless achieve effective collision avoidance.

Here, the protection zones 37 are shown as having a spherical shape. In order, optionally, to approach an object shape in a better way, however, it is also possible to use ellipsoids or other shapes.

Figure 7:
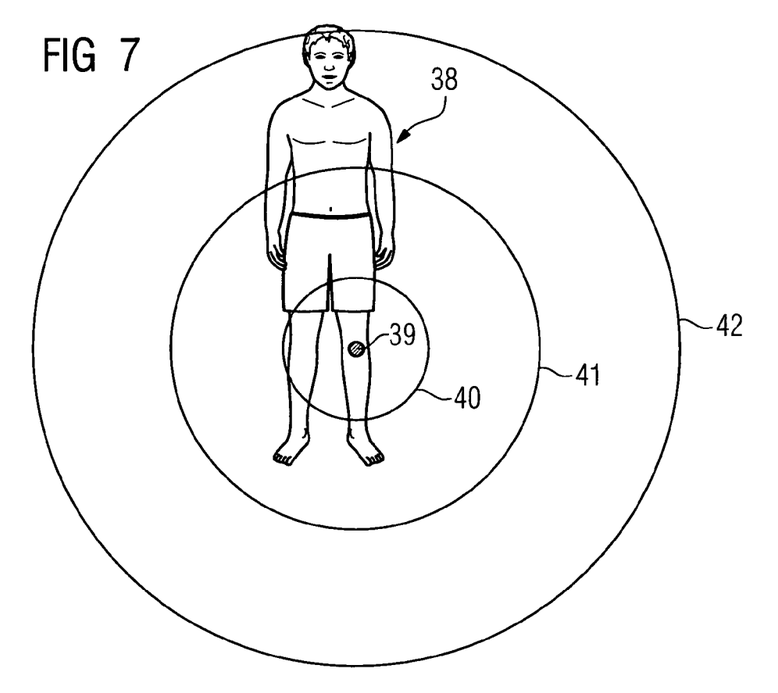

FIG. 7 shows a sketch for the definition of different limit values with a method according to the invention. Once again, this shows a mobile object 38 which is a person. The person is wearing a position sensor 39 in the region of the left leg. Arranged around the position sensor 39 are different protection zones 40, 41 and 42 corresponding to limit values for the movement monitoring. The protection zones can, for example, be arranged around the position sensor 39 in an ellipsoidal, or as shown here, circular shape. Correspondingly, in the three-dimensional area, ellipsoids or spheres or other shapes are defined in dependence on the shape of the mobile object 38 or the shape of the component of the mobile object 38 bearing the position sensor 39. In order, as in the case shown here, to protect a leg against collisions, it is worth considering the definition of cylindrical protection zones. The circular shape and the radii in the illustration shown here should, therefore, be understood to be examples only. In particular in cases when the object bears still further position sensors 39, small radii for the protection zones 40, 41, 42 are preferable in order not to restrict the possible movements in the medical installation unnecessarily.

If there is now another mobile or fixed object in the region of the protection zone 42, in the present case an acoustic alarm is triggered. This is a first warning for the operator or the person wearing the position sensor 39. If the mobile object 38 moves further toward another object or another object moves toward the mobile object 38 in such a way that the limit value assigned to the protection zone 41 is achieved or exceeded, the speed of movement of the other object, for example a part of an installation is reduced. When the protection zone 40 is reached, the movement is automatically stopped. This means that, in the case of an approach corresponding to the protection zone 40, the automatically controlled movement of, for example, a C-arm of an X-ray device is stopped in order to prevent a collision with the mobile object 38.

Figure 8:
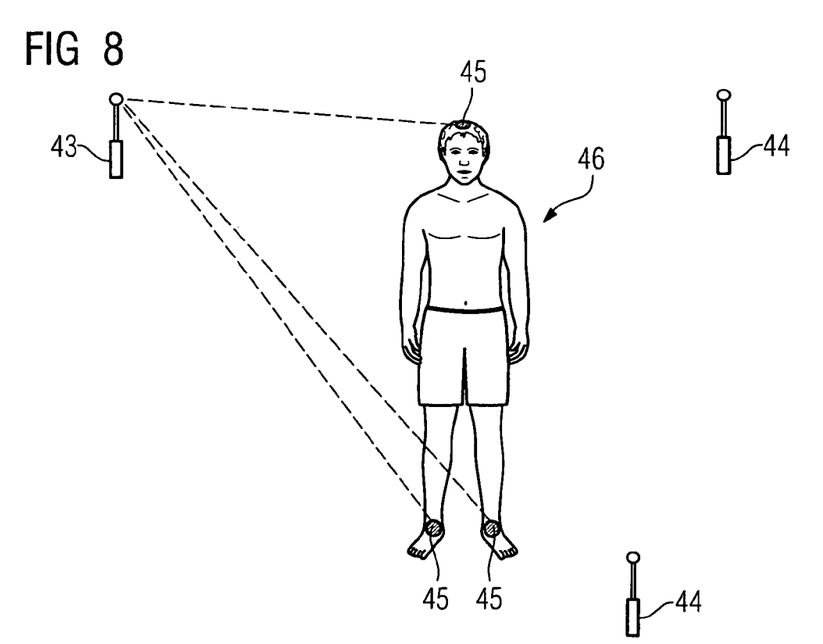

FIG. 8 illustrates how to increase the accuracy of the position detection with a method according to the invention, which is based on the fact that, in addition to a transmitting/receiving antenna 43 which is designed for the reception or transmission von RFID signals or RF energy for the purpose of position detection, still further alternative or additional transmitting/receiving antennas 44 are provided by means of which the accuracy of the position recognition can be improved if required. In addition, the additional transmitting/receiving antennas 44 ensure that the signals from the position sensors 45 are received in each case by at least one antenna. In the case shown, the position sensors 45 are arranged on a person 46, but they can also be arranged on other mobile objects such as installation parts or tool trolleys and the like.

The system of position sensors 45 and antennas 43, 44 enables the reliable three-dimensional spatial detection of objects in and hence their effective protection from collisions or from coming too close with or to other installation parts or people and the like. The position sensors 45 or movement sensors can be sensors on stickers or in arm straps or clips, plates and the like. Also suitable for people are sensors which are already incorporated in clothing. RFID sensors or transponders and corresponding reading devices work without cables and permit a relatively inexpensive implementation of the movement monitoring. However, it is also possible to use in this way or supplementary thereto position sensors 45 or transmitting and receiving units based on other principles, for example on optical or thermal principles of operation.

The invention claimed is:

1. A method for monitoring a movement of a mobile object in a medical installation, comprising:
    arranging a position sensor on the mobile object, wherein the mobile object is selected from the group consisting of: an X-ray system, a patient's bed, a respirator, a trolley, a tool table, an operator, and a patient;
    detecting a current three-dimensional position of the mobile object by the position sensor;
    determining a relative position of the mobile object to a further mobile object or a fixed object based on the detected position of the mobile object; and
    triggering an action if the relative position is smaller than a limit value for avoiding a collision between the mobile object and the further mobile object or the fixed object.

2. The method as claimed in claim 1, wherein the position of the mobile object is detected continuously or at time intervals.

3. The method as claimed in claim 1, wherein the position of the mobile object is detected by a receiving device based on a signal from the position sensor.

4. The method as claimed in claim 1, wherein the action is selected from the group consisting of: issuing an alarm, slowing down the movement of the mobile object, issuing a feedback at a user interface, stopping the movement of the mobile object, and performing a further measure for collision avoidance.

5. The method as claimed in claim 4, wherein a plurality of limit values for the relative position are determined and different measures for collision avoidance are performed based on the relative position and the limit values.

6. The method as claimed in claim 5, wherein the alarm is issued if the relative position is smaller than a first limit value, the movement of the mobile object is slowed down and the feedback is issued at the user interface if the relative position is smaller than a second limit value, and the movement of the mobile object is stopped if the relative position is smaller than a third limit value.

7. The method as claimed in claim 1, wherein the position sensor comprises a cableless position sensor.

8. The method as claimed in claim 1, wherein the position sensor is operated by a method selected from the group consisting of: a magnetic method, an electromagnetic method, an electric method, a capacitive method, an inductive method, an optical method, a thermal method, and an acoustic method.

9. The method as claimed in claim 1, wherein the position sensor is arranged on the mobile object by a method selected from the group consisting of: an adhesion surface, a label, a hook, a loop strap, a mechanical clamp, a clip, a screw, a pin, a needle, a hair pin, a strap, a sling-on strap, an aim strap, a spectacle frame, a clothing, a mouth guard, and a head cap.

10. The method as claimed in claim 1, wherein a plurality of position sensors are arranged on a plurality of mobile objects for detecting current three-dimensional positions of the mobile objects.

11. The method as claimed in claim 1, wherein the position of the mobile object is compared with movements of other components of the medical installation that are stored in a system control or actually moved movements and a measure for collision avoidance is performed based on the comparison.

12. The method as claimed in claim 1, wherein a receiving device is arranged on the mobile object and a measure for collision avoidance is performed based on a signal detected on the receiving device.

13. A medical installation, comprising:
    a mobile object, wherein the mobile object is selected from the group consisting of: an X-ray system, a patient's bed, a respirator, a trolley, a tool table, an operator, and a patient;
    a position sensor arranged on the mobile object that detects a current three-dimensional position of the mobile object; and
    an evaluation unit that:
        determines a relative position of the mobile object to a further mobile object or a fixed object based on the detected position of the mobile object; and
        triggers an action if the relative position is smaller than a limit value for avoiding a collision between the mobile object and the further mobile object or the fixed object.

14. The medical installation as claimed in claim 13, wherein the action is selected from the group consisting of: issuing an alarm, slowing down the movement of the mobile object, issuing a feedback at a user interface, stopping the movement of the mobile object, and performing a further measure for collision avoidance.

15. The medical installation as claimed in claim 14, wherein a plurality of limit values for the relative position are determined and different measures for collision avoidance are performed based on the relative position and the limit values.

16. The medical installation as claimed in claim 15, wherein the evaluation unit issues the alarm if the relative position is smaller than a first limit value, slows down the movement of the mobile object and issues the feedback at the user interface if the relative position is smaller than a second limit value, and stops the movement of the mobile object if the relative position is smaller than a third limit value.

* * * * *